United States Patent [19]

Lampinen et al.

[11] Patent Number: 5,454,264
[45] Date of Patent: Oct. 3, 1995

[54] BEARING CAPACITY MEASURING APPARATUS

[76] Inventors: Anssi Lampinen, Lämpömiehenkuja 2; Kimmo Simomaa, Metallimiehenkuja 8, both of SF-02150 Espoo, Finland

[21] Appl. No.: 75,592
[22] PCT Filed: Dec. 18, 1990
[86] PCT No.: PCT/FI90/00303
§ 371 Date: Jun. 15, 1993
§ 102(e) Date: Jun. 15, 1993
[87] PCT Pub. No.: WO92/11526
PCT Pub. Date: Jul. 9, 1992

[30] Foreign Application Priority Data

Sep. 12, 1989 [FI] Finland .................... 894307

[51] Int. Cl.⁶ ................................ G01N 3/00
[52] U.S. Cl. ........................ 73/12.06; 73/12.04
[58] Field of Search ................ 73/11.01, 12.01, 73/12.04, 12.06, 12.13, 78, 79, 84

[56] References Cited

U.S. PATENT DOCUMENTS 3,365,929 1/1965 Messner ...................... 73/12.04
3,425,263 2/1969 Elliot et al. .................. 73/12.13
3,453,862 7/1969 Elliot et al. .................. 73/12.13
3,888,108 6/1975 Brands ........................ 73/12.13

FOREIGN PATENT DOCUMENTS 3712455 10/1988 Germany .
3807065  4/1990 Germany .
60-73338  4/1985 Japan .
544304 11/1973 Switzerland .
849042  7/1981 U.S.S.R. .

Primary Examiner—Richard E. Chilcot, Jr.
Assistant Examiner—Ronald L. Biegel
Attorney, Agent, or Firm—Merchant, Gould, Smith, Edell, Welter & Schmidt

[57] ABSTRACT

The invention concerns a means for measuring bearing capacity, comprising a drop weight (1), drop weight holding and releasing means (2), and a measuring apparatus (3). As taught by the invention, the means comprises a tubular body (4) inside which the drop weight (1) is provided to be movable; a loading plate (5) closing the lower end of said body; and an acceleration pickup (6) disposed to measure the movement of the body during impact.

12 Claims, 1 Drawing Sheet

ACCELEROMETER

BEARING CAPACITY MEASURING APPARATUS

BACKGROUND OF THE INVENTION

The present invention concerns an apparatus for measuring bearing capacity.

It is frequently necessary in connection with the structural courses of roads and streets, of various building foundations and also with the filling of excavations, to measure the bearing capacity of such surfaces. The bearing capacity of roads is commonly measured using an apparatus in which a load is applied on the structure to be measured by a load equivalent to the rear wheels of a lorry (Benkelman beam, Lacroix deflection measuring car), in the form of static loading with the aid of a rigid loading plate (the plate loading test) or in the form of dynamic loading on a rigid plate with the aid of a drop weight (drop weight apparatus).

Existing apparatus have significant drawbacks: they are big, expensive and unwieldy in use, and therefore bearing capacity measurements on smaller objects are not feasible. An object of this kind is encountered e.g. on roads and streets in filling work on various excavations, which could by filling one course at a time, with intervening compaction and measurement using a suitable bearing capacity measuring means, be filled right away in one go in a manner precluding subsequent formation of holes or presence of residual eminences.

SUMMARY OF THE INVENTION

The object of the present invention is to eliminate the drawbacks mentioned above. It is a specific aim of the invention, to provide a novel, lightweight bearing capacity measuring apparatus which enables bearing capacity measurements to be made rapidly and with adequate accuracy, and which is easily transportable e.g. by carrying, from one point of measurement to another.

The bearing capacity measuring apparatus of the invention comprises a drop weight of suitable size, on the order of magnitude of e.g. 10 kg, holding and releasing members for the drop weight, and a measuring means for measuring the subsidence of the surface under measurement due to dropping the drop weight. As taught by the invention, the apparatus comprises a tubular body inside which a drop weight has been disposed to be substantially free to move in the direction of the tune. Furthermore, the lower end of the body is closed with a loading plate against which the drop weight is flung when it is allowed to drop freely within the body. As taught by the invention, the measuring means comprises an acceleration pick-up, for instance secured to the body, arranged to measure the movement of the tubular body of the apparatus during the impact. When an acceleration pick-up is used, the amount of movement, i.e., the magnitude of subsidence, is found by integrating the acceleration signal to give the velocity and, further, to give the displacement. It is possible of course to use a velocity pick-up or e.g. a seismic displacement pick-up instead of the acceleration pick-up.

The measuring means with its acceleration pick-up is advantageously placed in the upper part of the body, above the upper position of the drop weight, in which case the greater part of the measuring equipment consists of a hollow tube closed at both ends inside which the drop weight can move under gravity effect in one direction or the other, depending on the attitude of the tube.

It is advantageous to provide on the underside of the drop weight an elastic member, e.g. a rubber shock absorber, which prevents excessively abrupt and sharp impacts against the surface under measurement, whereby the impact will more closely correspond e.g. to those loads which cars cause on the road surface.

In an advantageous embodiment of the invention the holding and releasing member belonging in the upper part of the body consists of a magnet, its control, i.e., releasing of the drop weight, being arranged by an apparatus of an electric pulse which is delivered with a release push button external to the body. It is however equally possible to apply mechanical means for releasing/securing the drop weight.

When a magnet is used for releasing member, dropping the drop weight is accomplished with an electric pulse, with which the zero resetting of the apparatus is also accomplished, e.g. with a suitable delay, counted from the moment of release. In this way, resetting is achieved clearly after the weight has been set free and before it strikes against the loading plate, and the recoil from the release of the weight will have died out completely and will not cause any measuring error.

The apparatus here described is meant to be portable so that it can be carried in the terrain, which implies that normally no external electricity supply is available. The release pulse, e.g. 24 V, which the release magnet requires is advantageously obtained e.g. from three 9 V press-button batteries connected in series, which store a release charge e.g. through a 600 ohm resistance e.g. in a 2200 microfarad electrolytic capacitor, which is discharged through the solenoid of the magnet at the moment of release. The rapidly dying pulse shape appearing across the magnet terminals is also appropriate to be used towards the base zero-setting of the electronics just before impact. The measuring electronics is advantageously constructed applying low-consumption CMOS technique, and a liquid crystal display (LCD) is advantageous in the role if display means.

The body consists, advantageously, of a tube of some light material, for instance an aluminum tube. The apparatus itself will thereby have the lowest possible weight and the drop weight alone has a large enough mass. Therefore, the inertia of the rest of the measuring apparatus has no great influence on the measurement.

The body advantageously comprises at least one handle, suitably two separate carrying handles, by which the measuring apparatus can be transported and by which it can be upended with ease so that the drop weight is made to slide inside the body, from the lower to the upper position.

In an advantageous embodiment of the invention the acceleration pick-up is in the upper part of the body, surrounded with a suitable, thin and elastic layer, e.g. a rubber sheath, which appropriately damps excessive, sharp motions acting on the pick-up and thus increases the uniformity and accuracy of the measurements.

In an advantageous embodiment of the invention holes have been provided in the tubular body, through which air can flow as the drop weight is moving within the tubular body. The drop weight may likewise contain suitable air passages running parallel to its direction of motion. It has been found in practice, however, that the drop weight falls substantially with complete freedom through the distance of about 1 m in the tubular body and against the loading plate even in the absence of air holes, provided that the drop weight has been dimensioned so as to leave a gap of a few millimeters between itself and the tubular body.

In an advantageous embodiment of the invention the loading plate is exchangeable, or it is possible to attach to it, e.g. on its outside, plates with various areas, whereby different kinds of measurement can be made using one drop weight. It is equally possible to use, instead of said plates, bodies of various shapes which represent load modes encountered in actual situations, such as a horseshoe, when it is desired to measure bearing capacities of a horse race track, for instance.

The advantage of the invention over bearing capacity measuring apparatus of prior art is in the first place seen in the simple and lightweight construction of the present apparatus, which enables its easy and fast use, and transportability, also in small and cramped applications.

BRIEF DESCRIPTION OF THE DRAWINGS

The invention is described in the following in detail, referring to the attached drawing, wherein.

DETAILED DESCRIPTION OF THE PREFERRED EMBODIMENT

Figure 1:
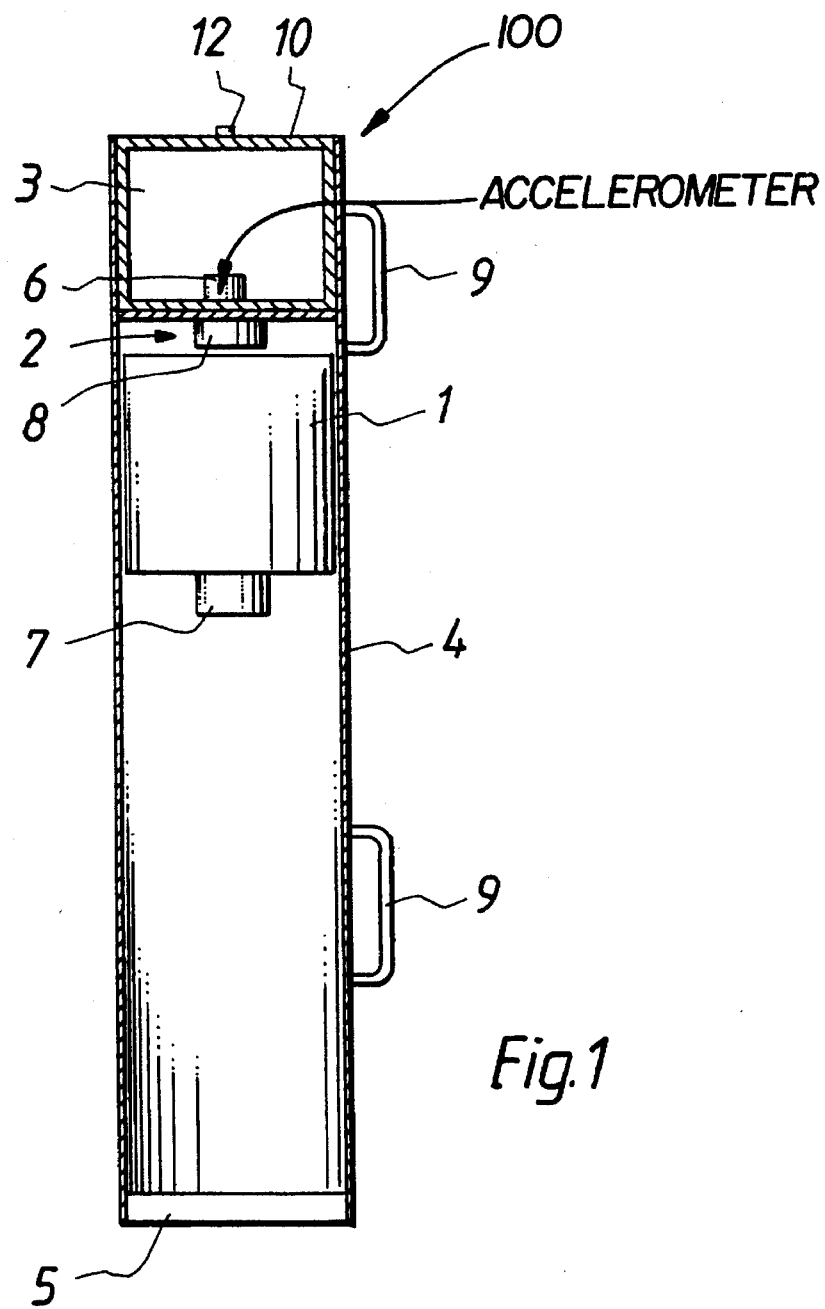
FIG. 1 presents schematically and in elevational view, a bearing capacity measuring apparatus according to the invention.
Figure 2:
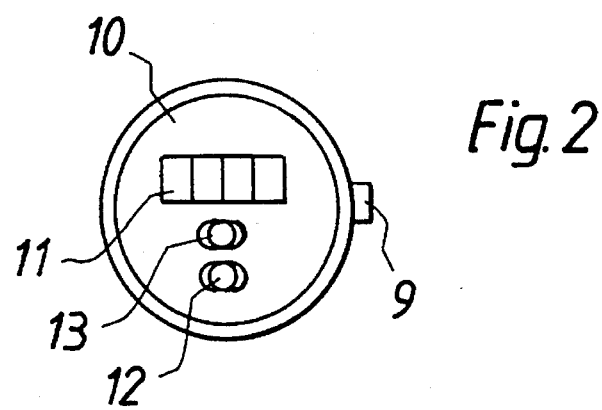
FIG. 2 presents the apparatus of FIG. 1, in a top view.

A bearing capacity measuring apparatus 100 according to the invention, depicted in the drawing, comprises a circular cross-section, tubular body 4 closed at the lower end by a loading plate 5 and at the top end by the measuring means 3. Between these, there is a substantially free, rectilinear tubular cavity with a length about 80 to 90% of the overall length of the apparatus 100. A cylindrical drop weight 1 having a diameter slightly less than the inner diameter of said cavity is disposed inside the tubular body 4, and a rubber pad, serving as resilient member 7, is disposed on the underside of the drop weight 1. On the bottom of the measuring means 3 are affixed holding and release members 2, in the present embodiment consisting of a magnet 8 with high enough attraction to be able to hold the drop weight 1 stationary.

The measuring means 3 comprises an acceleration pick-up 6, braced against the tubular body 4 of the measuring apparatus 100, and hereby it measures the movement of the apparatus 100 as the drop weight 1, after free fall, strikes against the loading plate 5.

On the cover 10 of the apparatus 100 is provided a display means 11, and a power switch 13 and release button 12. The measuring apparatus 100 further comprises two carrying handles 9, one in the upper part and the other in the lower part of the measuring apparatus 100.

The bearing capacity measuring apparatus 100 of the invention is operated as follows. When measuring the bearing capacity of a substantially horizontal surface, the measuring apparatus 100 is placed in a vertical position on this surface, with the loading plate 5 against the point to be measured. With the drop weight 1 in its upper position, as in FIG. 1, the power switch 13 is switched on, and thereafter the release button 12 is pressed to produce a release pulse acting on the magnet 8, which releases the drop weight 1, which thus allows the drop weight to drop freely within the tubular body 4 towards the loading plate 5. The impact of the drop weight against the loading plate 5 causes downward depression of the surface that is being measured, at the same time causing the tubular body 4 of the apparatus 100 to descend an equal amount, this displacement being measured with the aid of the acceleration pick-up 6 in a manner known in itself in the art. Since as a rule the surface under measurement is resilient, the surface, and at the same time the apparatus 100, will rebound a certain distance upward. Advantageously, as taught by the invention, the measurement is accomplished as a continuous measurement so that in one measurement is measured the total displacement of the tubular body 4 of the apparatus 100 during the impact, that is, the permanent as well as the elastic compaction of the test surface during impact. The user has the option of getting as measurement output e.g. only the highest values of the permanent and elastic compactions, or the curve pattern of the whole compaction event during impact, in other words, the compaction during impact as a function of time.

When a repeat measurement is desired, the measuring apparatus 100 is held by the carrying handles 9 and inverted, whereby the drop weight 1 is returned into contact with the magnet 8 and made adherent thereto. The measurement may then be repeated. Zero-setting of the measuring means 3 is provided e.g. in connection with the release button 12 so that on pressing this button, i.e. just before the drop weight strikes against the loading plate 5, the measuring means 3 will be reset to zero.

In the foregoing, the apparatus 100 has been described in detail with reference to an advantageous structural design thereof, while various embodiments of the invention are feasible within the scope of the inventive idea delimited by the claims following below.

We claim:

1. An apparatus for measuring bearing capacity of a surface, comprising:

a tubular body, the tubular body being removably mounted on one of a plurality of loading plates, each of the plurality of loading plates having a different size and/or shape;

a drop weight being disposed inside the tubular body, the drop weight moving in a longitudinal direction of the tubular body;

the loading plate being mounted at a lower end of the tubular body so that the loading plate is in contact with the surface, the drop weight striking against the loading plate when the drop weight drops towards the loading plate; and means for measuring displacement of the surface which is stricken by the drop weight and the loading plate, the measuring means being mounted on an upper position of the drop weight.

2. An apparatus according to claim 1, further comprising a resilient member, the resilient member being disposed on a bottom side of the drop weight.

3. An apparatus according to claim 1, further comprising a resilient member, the resilient member being disposed on a top side of the loading plate.

4. An apparatus according to claim 1, further comprising means for holding and releasing the drop weight, the holding and releasing means including a magnet, the magnet releasing the drop weight when the holding and releasing means receives an electric pulse, the magnet holding the drop weight to prevent the drop weight from dropping towards the loading plate when the holding and releasing means does not receive the electric pulse.

5. An apparatus according to claim 1, wherein the tubular body is made of aluminum.

6. An apparatus according to claim 1, wherein the tubular body includes at least one handle.

7. An apparatus according to claim 6, wherein one handle is disposed at a distance from the lower end of the tubular body, so that when the apparatus is carried by the handle, the apparatus is balanced with the drop weight against the loading plate.

8. An apparatus according to claim 6, further comprising a cover at an upper end of the tubular body, the cover including a drop weight release button and display means for displaying the displacement.

9. An apparatus according to claim 1, wherein the acceleration pick-up is surrounded with a resilient layer.

10. An apparatus according to claim 1, wherein the tubular body and the drop weight defines an air passage to enable free air flow while the drop weight is being dropped.

11. An apparatus according to claim 1, wherein the acceleration pick-up measures the displacement of the tubular body during impact as a continuous function.

12. An apparatus according to claim 1, wherein the loading plate is attached to the surface.

* * * * *

UNITED STATES PATENT AND TRADEMARK OFFICE
CERTIFICATE OF CORRECTION

PATENT NO. : 5,454,264

DATED : October 3, 1995

INVENTOR(S) : Anssi Lampinen, et al.

It is certified that error appears in the above-indentified patent and that said Letters Patent is hereby corrected as shown below:

In column 3, line 43, delete "6," and insert --6. The measuring means 3 is--.

In column 3, line 44, after "hereby", delete "it" and insert --the acceleration pick-up at 6--.

In claim 2, line 2, delete "disposed" and insert --mounted--.

In claim 3, line 2, delete "disposed" and insert --mounted--.

In claim 9, line 2, after "pick-up" insert --means--.

In claim 11, line 1, after "the" insert --measuring means includes an--; and in line 2, after "pick-up" delete "measures the" and insert --means for measuring a--.

Signed and Sealed this

Sixth Day of August, 1996

Attest:

BRUCE LEHMAN

Attesting Officer

Commissioner of Patents and Trademarks